US010294522B2

(12) United States Patent
Gajewski et al.

(10) Patent No.: US 10,294,522 B2
(45) Date of Patent: May 21, 2019

(54) SAMPLE HANDLING SYSTEM WITH DOSING DEVICE AND THERMAL CYCLER

(71) Applicant: HAMILTON Bonaduz AG, Bonaduz (CH)

(72) Inventors: Martin Gajewski, Leichlingen (DE); Mario Arangio, Chur (CH)

(73) Assignee: HAMILTON BONADUZ AG, Bonaduz (CH)

( * ) Notice: Subject to any disclaimer, the term of this patent is extended or adjusted under 35 U.S.C. 154(b) by 481 days.

(21) Appl. No.: 14/150,041

(22) Filed: Jan. 8, 2014

(65) Prior Publication Data

US 2014/0193826 A1  Jul. 10, 2014

(30) Foreign Application Priority Data

Jan. 9, 2013  (DE) .................. 10 2013 200 193

(51) Int. Cl.
*C12Q 1/68* (2018.01)
*G01N 35/10* (2006.01)
(Continued)

(52) U.S. Cl.
CPC ......... *C12Q 1/686* (2013.01); *G01N 35/0099* (2013.01); *G01N 35/028* (2013.01);
(Continued)

(58) Field of Classification Search
CPC .................. B01L 3/50851; B01L 7/54; G01N 2035/00306; G01N 2035/00316
See application file for complete search history.

(56) References Cited

U.S. PATENT DOCUMENTS 5,443,791 A    8/1995  Cathcart et al.
5,720,406 A *  2/1998  Fassbind ............. B01L 3/50851
                                         220/23.4
(Continued)

FOREIGN PATENT DOCUMENTS

DE        200 06 548 U1   9/2001
DE    10 2005 049 920 A1   4/2007
(Continued)

OTHER PUBLICATIONS

German Search Report dated Mar. 22, 2013 with English translation, 7 pages.
(Continued)

*Primary Examiner* — Kathryn Wright
(74) *Attorney, Agent, or Firm* — Rothwell, Figg, Ernst & Manbeck, P.C.

(57) ABSTRACT

A sample handling system and a process for the handling of chemical or biological samples is provided. The system includes a dosing device with a receiving plate configured in an essentially horizontal position in a plane defined by a first and a second axis. The dosing device has at least one working arm that is movable. The pipetting mechanism includes at least one pipetting channel that is movable and has a pipette tip mounted or mountable thereon. The system further includes at least one thermal cycler provided in the area of the receiving plate. The thermal cycler is configured on the receiving plate in such a way that the pipetting mechanism is movable in a position above the sample vessels in the thermal cycler, in a setting that allows a pipetting step to be carried out into the sample vessels in the thermal cycler by the pipetting mechanism in the position above the sample vessels in the thermal cycler.

21 Claims, 4 Drawing Sheets

(51) Int. Cl.
*C12Q 1/686* (2018.01)
*G01N 35/00* (2006.01)
*G01N 35/02* (2006.01)

(52) U.S. Cl.
CPC ... *G01N 35/10* (2013.01); *G01N 2035/00346* (2013.01); *G01N 2035/1051* (2013.01)

(56) References Cited

U.S. PATENT DOCUMENTS

| | | | |
|---|---|---|---|
| 6,197,572 B1* | 3/2001 | Schneebeli | B01L 3/50851 435/286.2 |
| 6,569,620 B1 | 5/2003 | Gold et al. | |
| 6,656,724 B1* | 12/2003 | Heimberg | G01N 35/0099 422/561 |
| 2004/0166513 A1* | 8/2004 | Slepnev | C12Q 1/6851 435/6.14 |
| 2009/0158863 A1* | 6/2009 | Shanafelter | G01N 35/021 73/864.81 |
| 2010/0227383 A1 | 9/2010 | Amano et al. | |
| 2012/0100600 A1* | 4/2012 | Slepnev | G01N 35/0099 435/287.2 |
| 2013/0196422 A1* | 8/2013 | Wilson | B01L 3/5085 435/289.1 |

FOREIGN PATENT DOCUMENTS

| | | |
|---|---|---|
| EP | 1 032 839 B2 | 10/2006 |
| EP | 1 508 809 B1 | 2/2007 |
| EP | 1 582 874 B1 | 7/2008 |
| WO | 9926070 A2 | 5/1999 |
| WO | 0177689 A1 | 10/2001 |
| WO | 20051059567 A1 | 6/2005 |

OTHER PUBLICATIONS

European Search Report issued in European Application No. 14 15 0467, dated Nov. 15, 2017, 6 pages.

* cited by examiner

SAMPLE HANDLING SYSTEM WITH DOSING DEVICE AND THERMAL CYCLER

CROSS REFERENCE TO RELATED APPLICATION

This application claims the benefit of German Patent Application No. 10 2013 200 193.2 filed on Jan. 9, 2013, the disclosure of which is incorporated herein in its entirety by reference.

The present invention concerns a sample handling system for the handling of chemical or biological samples, particularly body fluids such as blood, saliva, secretions, etc. or tissue samples, more specifically for the handling of samples for DNA analysis by means of PCR, and a process for controlling said sample handling system.

The sample handling system comprises a dosing device
- with a receiving plate, wherein the receiving plate is configured in an essentially horizontal position in a plane defined by a first and a second axis (X, Y); and
- with at least one working arm that is movable in the direction of the first axis (X) relative to the receiving plate (14), preferably along a first edge of the receiving plate, wherein the working arm extends along the second axis (Y) above the receiving plate, at least one pipetting mechanism that is movable at least in the direction of the second axis (Y) is mounted on the receiving arm, the pipetting mechanism comprises at least one pipetting channel that is movable in the direction of a third axis (Z) orthogonal to the direction of the first and second axes (X, Y) and has a pipette tip mounted or mountable thereon, and the pipetting mechanism is configured so as to dispense or aspirate liquid into or out of a sample vessel;
- and at least one thermal cycler that is provided in the area of the receiving plate.

For example, a sample handling system of this type is known from WO 99/260070A2.

Moreover, another system is known under the name "epMotion 5075 MC," manufactured by the firm Eppendorf AG (cf. www.eppendorf.com/int/index.php?pb=25118564b687acb3&page=3&action=epmotion&contentid=3&page=8).

Both of the sample handling systems known in prior art may be configured with a waste receptacle for used pipette tips, a mixing/shaking device, etc., and a thermal cycler in the area of the receiving plate. However, this thermal cycler can be automatically equipped with pre-filled sample vessels on its sample vessel carriers (PCR plates, etc.) only by means of a gripper. In both of the sample handling systems known in prior art, importance is placed on configuring the thermal cycler and the pipetting mechanism with spatially separated workstations. Ordinarily, sample vessels or sample vessel carriers used in PCR process steps are placed in the thermal cycler in sealed form, and the thermal cycler is then sealed with a lid. It is not possible to add or remove sample liquid during processing steps in the thermal cycler.

The purpose of the invention is to further develop a sample handling system known in prior art so as to allow more flexible handling during the processing of samples.

For this purpose, the invention provides a system in which the thermal cycler is placed on the receiving plate in such a manner that the pipetting mechanism is movable above the sample vessels inside the thermal cycler in a position that allows a pipetting step to be carried out.

This provides the advantageous possibility of conducting pipetting steps during and/or between the process steps that must be carried out in the thermal cycler without requiring that the sample vessels (also referred to as wells) or the accompanying sample vessel carrier (for example, a so-called PCR plate provided with wells) be removed from the thermal cycler and transported to a pipetting position on the receiving plate. It is therefore extremely simple to add a further reaction component to the sample liquid (also known as a PCR reaction mixture) heated in the thermal cycler without requiring that the samples be cooled off and then reheated to the desired temperature in a pipetting step that takes place outside the thermal cycler. In particular, this provides simplified handling overall, particularly in the case of PCR processes, because all of the cycles required for PCR processes in the thermal cycler can be run and the components required for certain process steps can be added to the samples by means of the pipetting mechanism without requiring that the sample vessels or their sample vessel carrier be removed from the thermal cycler. This results in improved automation of processing and thus saves time, specifically because transportation steps between the thermal cycler and the pipetting position on the receiving plate and lengthy temperature control steps in which a sample vessel carrier (PCR plate) must be removed from the thermal cycler and subsequently reused are eliminated.

Of course, the pipetting mechanism can carry out other pipetting steps concurrently outside the thermal cycler while the thermal cycler completes cycles, such as preparation of a subsequent batch of sample vessels for a subsequent process in the thermal cycler.

It is further recommended that the sample handling system include a control mechanism that is configured to activate or control functions of the dosing device such as movement in the directions of the three axes and/or aspiration or dispensing of liquid by means of the pipetting mechanism and functions of the thermal cycler such as conducting cycles in a PCR process. This kind of control mechanism can consist of a computer with corresponding control programs. It is also possible for the control mechanism to comprise a plurality of mutually networked computers, for example a processor for the pipetting mechanism and a processor for the thermal cycler.

According to one embodiment, the thermal cycler can be placed on the receiving plate, wherein a highest point of the thermal cycler is located below a maximum possible interval between a lower end of at least one pipette tip and the receiving plate, with the interval making it possible for the pipetting mechanism to move in the direction of the third axis (Z).

As an alternative to this, it is recommended that a thermal cycler be mounted in a notch made in the receiving plate in such a manner that a lower surface of the thermal cycler is positioned below the receiving plate and a highest point of the thermal cycler is located below the maximum possible interval between a lower end of at least one pipette tip and the receiving plate, with the interval making it possible for the pipetting mechanism to move in the direction of a third axis (Z).

For both embodiments, it is preferred that the maximum interval between the lower end of at least one pipette tip and the receiving plate be approximately 100 mm to 180 mm, and more preferably approximately 125 mm to 150 mm.

The maximum interval between the receiving plate and the lower end of at least one pipette tip can also be referred to as maximum overrun height. If an object placed in the area of the receiving plate is higher than this maximum interval, it will constitute an obstacle for the pipetting mechanism, which then cannot be moved in this area or can be moved only if no pipetting tip is installed on the pipettes. Although such objects can be placed on the receiving plate, they must then be taken into consideration in controlling the movement of the pipetting mechanism so as to prevent collisions.

As a rule, thermal cyclers known in the art have a construction height that is greater than the aforementioned maximum interval between the pipette tip and the receiving plate. An existing thermal cycler can therefore be used, preferably in accordance with the embodiment, with a notch being made in the receiving plate in which the thermal cycler known in the art is mounted.

Preferably, a thermal cycler conforming to the pipetting mechanism and the aforementioned maximum interval between the pipette tip and the receiving plate should be used, with said thermal cycler constituting a module that supplements the dosing device and, like other components of the dosing device, such as a waste receptacle, mixing device, etc., can be configured at a desired position on the receiving plate.

The thermal cycler is preferably provided with a lid-like closing device for covering the vessels inside the thermal cycler, wherein the closing device is movable relative to the thermal cycler in a direction that is essentially parallel to the receiving plate between an open setting in which the interior of the thermal cycler is freely accessible and a closed setting in which the interior of the thermal cycler is covered. This kind of closing device does not protrude in its open setting upward into the area in which the pipetting mechanism and pipette tips attached to it move. Free access of the pipetting mechanism to sample vessels in the thermal cycler is therefore supported.

It is further recommended that the control mechanism be configured such that the closing device of the thermal cycler is moved into its open or closed setting depending on the position of the pipetting mechanism relative to the thermal cycler, preferably such that the closing device is moved to its open setting when a step of pipetting into the sample vessels inside the thermal cycler is carried out by means of the pipetting mechanism and such that the closing device is moved to its closed setting after the step of pipetting into the sample vessels inside the thermal cycler is completed.

This kind of control makes it possible to open the thermal cycler shortly before the actual pipetting step, so that the cooling temperature effects of the environment in particular can be reduced. It is also possible that after a pipetting step, for example the simultaneous dispensing of one component into a plurality of sample vessels, the closing device is briefly returned to its closed setting by the pipetting mechanism until the used pipette tips have been disposed of in the waste receptacle, new (unused) pipette tips have been obtained, and the component to be dispensed has been aspirated from a reserve container. As soon as the pipetting mechanism containing unused pipette tips filled with the component is on the way to the thermal cycler, the closing device can be moved back to its open setting so that the component can be dispensed into a subsequent series of a plurality of sample vessels. Of course, it is also conceivable for the closing device to be opened in each case far enough to make only those vessels accessible into which a component is to be dispensed or from which sample liquid is to be aspirated. Such a partial release of the sample vessels can also be understood to constitute an open setting. This can be achieved, for example, by means of a two-part closing device in which a gap can be left between the two movable closing device parts if needed, allowing free access to a plurality of sample vessels in the gap.

The sample handling system preferably includes a gripping mechanism that is movable relative to the receiving plate in the directions of the first, second, and third axes, driven by the control mechanism, and configured so as to pick up sample vessel carriers and transport them to desired locations on the receiving plate.

For this purpose, it is recommended as a further embodiment that the gripping mechanism be configured so as to move sample vessels in or remove sample vessels from the thermal cycler.

Another possibility in this case is that the gripping mechanism may be installed on the working arm or on an additional working arm that is movable relative to the receiving plate.

It is to be noted, for example, that corresponding drive components, including accompanying gear units, such as electric motors, hydraulic or pneumatic power units, and the like can of course be provided on the sample handling system in order to enable the desired movements of the dosing device, gripping mechanism, closing device of the thermal cycler, etc. These drive components should preferably be activated by the control mechanism.

The object of the invention is further achieved by means of a process for controlling the sample handling system presented above, wherein said process comprises the following steps:

opening of the closing device of a first thermal cycler;

removal of a sample vessel carrier containing sample vessels in the first thermal cycler by means of the gripping mechanism, with the sample vessels either filled with sample liquid or unfilled;

if applicable, filling of the sample vessels with sample liquid to be analysed by means of the pipetting mechanism;

preferably, filling of the sample vessels with further components required for analysis, such as a primer, polymerase, water, etc. by means of the pipetting mechanism;

conducting a PCR process, wherein the closing device of the first thermal cycler is opened or closed depending on the steps of the PCR process to be conducted, and wherein, depending on the setting of the closing device, at least a further component is dispensed by the pipetting mechanism to the sample vessels inside the first thermal cycler.

The recommended process makes it possible to pipette liquids or (reaction) components while the sample vessels are inside a thermal cycler that can be automatically opened or closed using the closing device. Pipetting steps therefore take place with the closing device set to the open position. Of course, the closing device is also opened in order to remove a sample vessel container after a PCR process is completed without a subsequent pipetting step. This means that the connection between the setting of the closing device and a pipetting step is not to be understood as meaning that a pipetting step must take place every time the closing device is opened. Rather, a pipetting step may take place with the closing device set to an open position if this is necessary for the PCR process.

Moreover, the process may also include the preferably automatic placement or removal of a sealing element that seals the sample vessels, such as a sealing mat, etc., on the sample vessel carrier depending on the PCR process and the setting of the closing device.

This kind of sealing element prevents the evaporation of sample liquid or readily volatile components of a sample to be analysed if these are heated to temperatures of approximately 95° C. during the PCR process. This kind of sealing element is to be removed prior to a pipetting step that preferably takes place automatically, for example by means of the gripping mechanism or a mechanism specifically designed for this purpose that is provided in the sample handling system.

After completion of a specified step of the PCR process, the closing device of the first thermal cycler may be opened, the sealing element preferably configured on the sample vessels may be removed, and processed sample liquid from the sample vessels may be aspirated by means of the pipetting mechanism and dispensed into additional, preferably empty sample vessels outside of the first thermal cycler, with the other sample vessels preferably being arranged in a sample vessel carrier that is preferably configured in a second preferably adjacent thermal cycler or on the receiving plate.

The process may also comprise: dispensing of a further component into the sample vessels contained in the first and/or second thermal cycler by means of the pipetting mechanism, with said pipetting step being followed by placement of the sealing elements on the sample vessels, closing of the closing device of the first and/or second thermal cycler, and carrying out of further steps of the PCR process.

In the following, the invention will be described using an example of a preferred embodiment in a manner that does not limit the scope of the invention.

Figure 1:
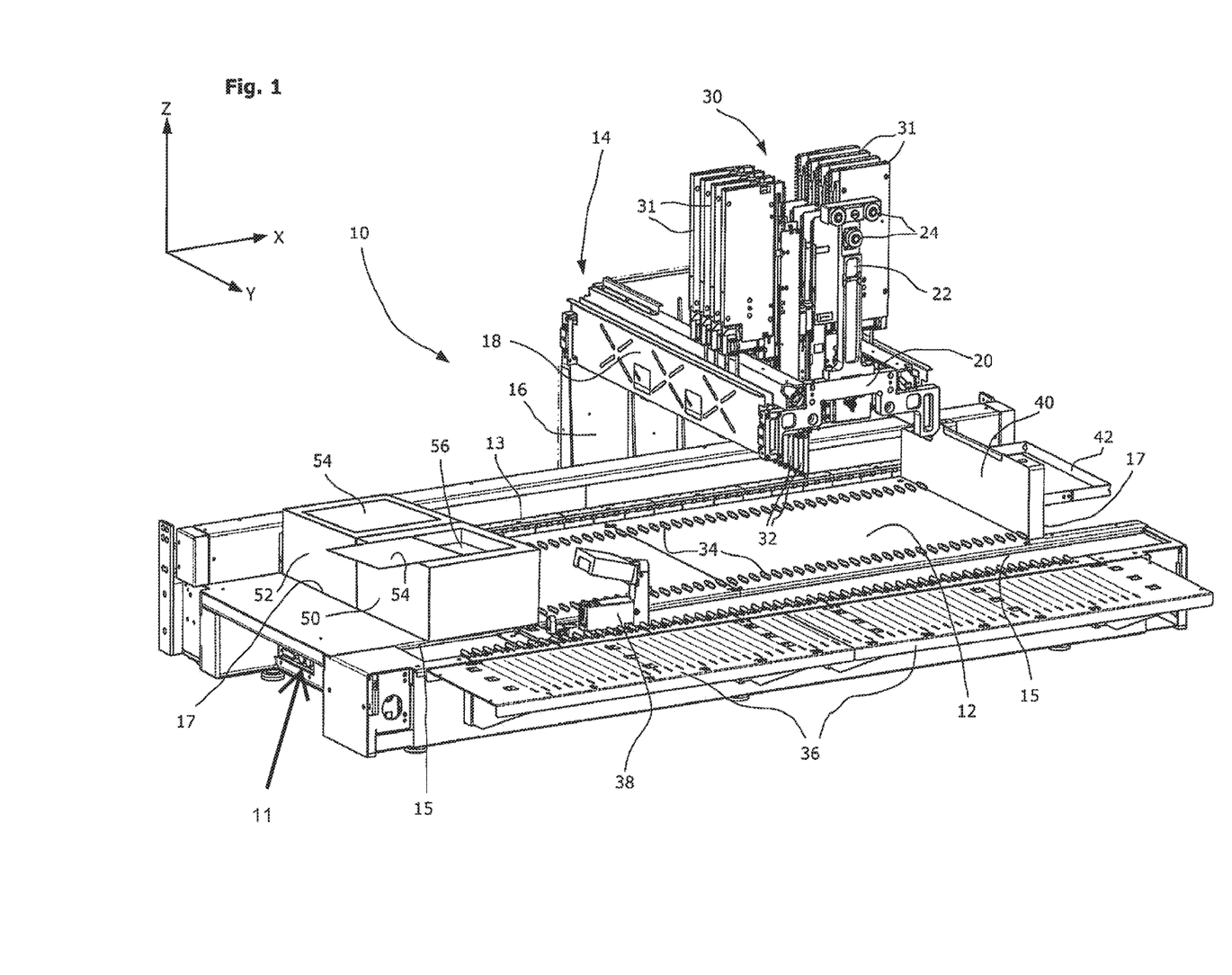
FIG. 1 shows a simplified schematic perspective view of an embodiment of a sample handling system.

FIG. 1 shows an embodiment of the sample handling system 10. It comprises a receiving plate 12 and a working arm 14 that is movable in the direction of a first axis X along a rear edge 13 of the receiving plate. The working arm 14 comprises a carrier 16 extending in the direction of a third axis Z and an extension arm 18 mounted on the carrier 16. The extension arm 18 extends in the direction of a second axis Y above the receiving plate 12. At the front end 20 of the extension arm 18 one can see a suspension bracket 22 with rollers 24 that are arranged in corresponding guide elements not shown here.

On the working arm 12, specifically on its extension arm 18, a plurality of pipetting units 31 that are part of the entire pipetting mechanism 30 are provided, each having a respective pipetting channel 32. In FIG. 1, for reasons of clarity, only four pipetting units 31 each are shown in the direction of the X axis on both sides of the extension arm. As a rule, up to eight pipetting units 31 may be provided on one side of the extension arm 18. The shown pipetting channels 32, at least the front four in the direction of the Y axis, are shown without the accompanying pipetting unit 31. The number of pipetting units 31 is determined according to a desired configuration of the pipetting mechanism 30 or the entire sample handling system 10; it is also possible for a pipetting mechanism 30 to be provided on only one side of the extension arm 18. The pipetting units 31 are moveable along the extension arm 18 in the direction of the Y axis, and the pipetting channels 32 are also movable in the direction of the Z axis.

The receiving plate 12 is equipped at regular intervals with guide elements 34, on which sample vessel carriers (e.g. carriers for test tubes, PCR plates, etc.), carriers for unused disposable pipette tips, reserve containers for reaction components to be pipetted, etc. can be installed in a slot/line configuration. Along a front edge 15 of the receiving plate, carrier plates 36 are installed, on which for example sample vessel carriers can be provided, which can then be moved by means of an automatic assembly unit 38 (if applicable, with a bar code reader, etc.) on the receiving plate 12 (in the direction of the Y axis).

The area of the receiving plate 12 that can be used, and specifically accessed, by the pipetting mechanism 30 is formed by the rear edge 13, the front edge 15, and the lateral edges 17. The pipetting mechanism 30 can be moved specifically over the right edge 17 in the direction of the X axis, allowing disposable pipette tips to be disposed of behind a separating element 40 in a waste receptacle (not shown) placed in a holder 42.

In the sample handling system 10, two thermal cyclers 50, 52 are shown as an example in purely schematic fashion on the left edge 17 of the receiving plate. The thermal cyclers 50, 52 are placed in the useful area of the receiving plate 12. Each of the thermal cyclers 50, 52 has one closing device 54 that is preferably movable parallel to the receiving plate 12 between an open setting and a closed setting. For the thermal cycler 50, the closing device 54 is shown in an approximately half-open setting. The thermal cycler 52 shows the closing device 54 in its closed setting. The thermal cyclers 50, 52 may contain sample vessel carriers such as PCR plates, which are not shown, in an interior space 56 in order to process samples contained in respective sample vessels (wells), for example in a PCR process.

Figure 2:
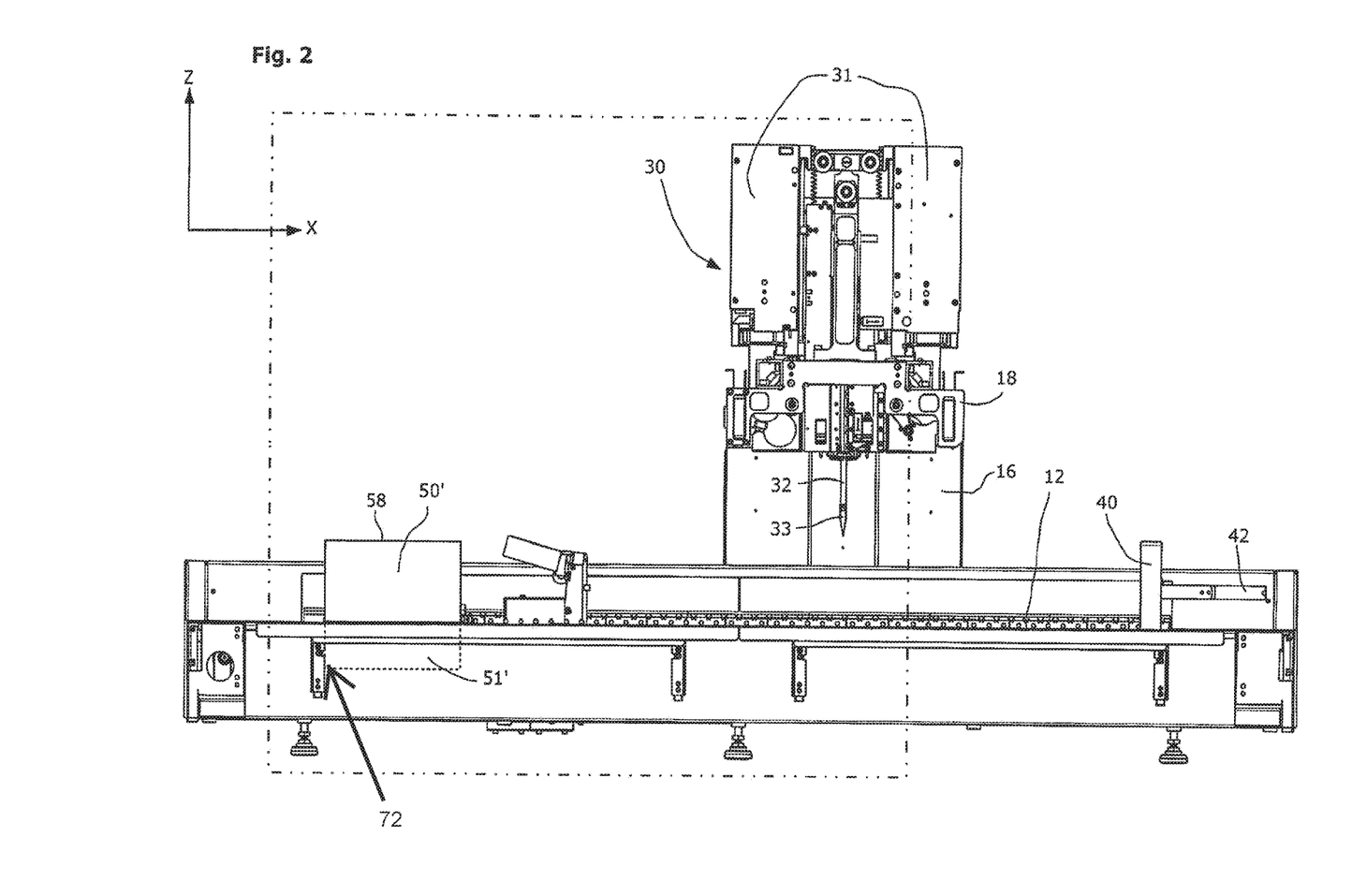
FIG. 2 shows the sample handling system in a cross-sectional view from the front in the direction of the second (Y) axis.
Figure 3:
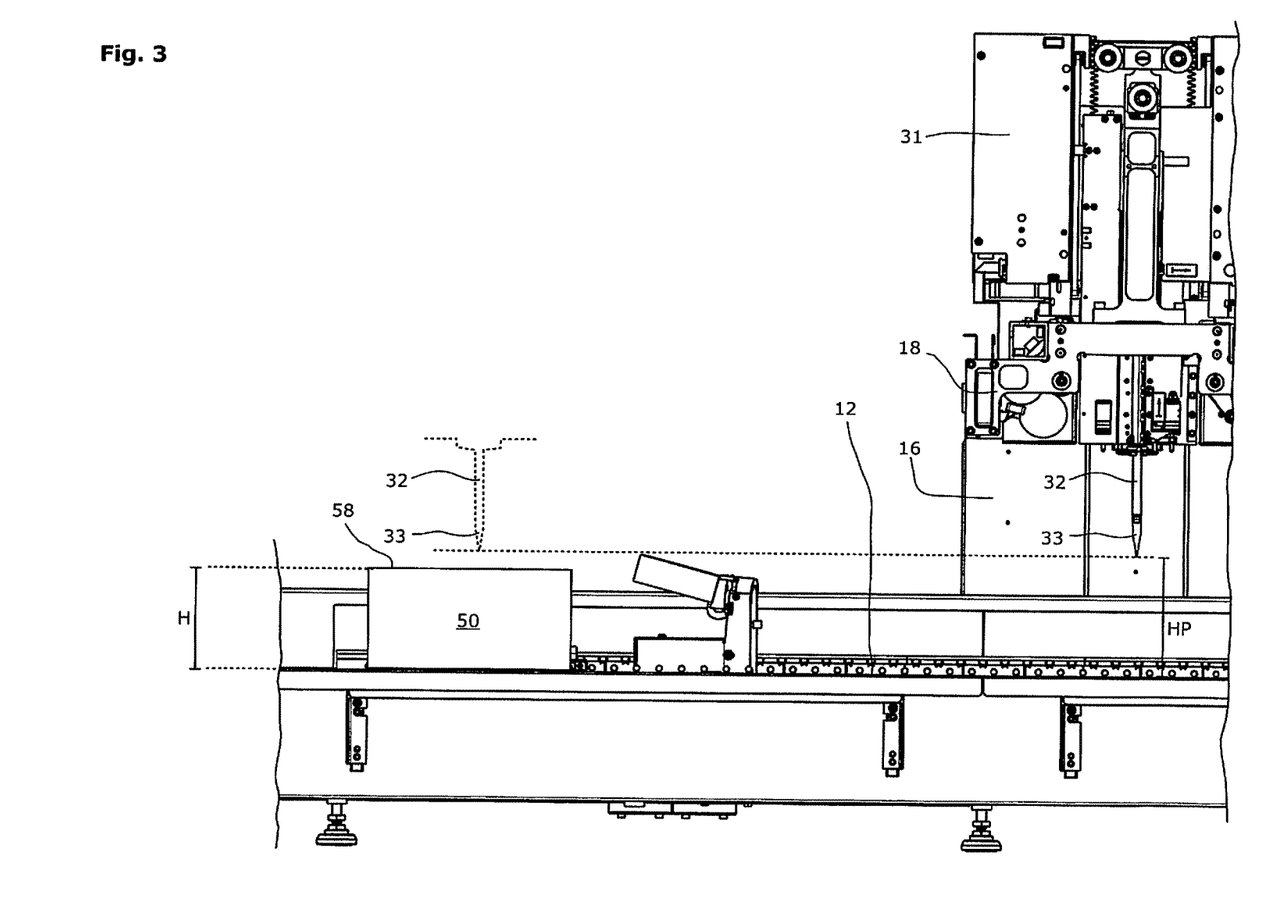
FIG. 3 shows an enlarged partial view of FIG. 2 corresponding to Area III indicated by dashed and dotted lines.

Referring to the sectional view of FIG. 2 and the enlarged section of FIG. 3, it can be seen that the thermal cycler 50 shows a highest point 58 or maximum height H above the receiving plate 12. This height (interval) H between the highest point 58 or the upper surface of the thermal cycler 50 and the receiving plate 12 is smaller than a maximum possible interval HP of a lower end of a pipette tip 33 that is attached to a pipetting channel 32. This allows the pipetting mechanism 30 to be used to conduct pipetting steps into sample vessels inside the thermal cycler 50. The interval HP between the receiving plate 12 and the pipette tip 33 can also be referred to as the overrun height. The intervals H and HP shown in FIG. 3 are purely schematic and given by way of example only. The difference between these two intervals can also be smaller. As a rule, it is assumed that the difference between the intervals H and HP is a few millimetres, and preferably less than 5 millimetres. The thermal cycler 50 or 52 is therefore configured on the receiving plate in such a manner that the pipetting mechanism 30 (with pipetting channel 32 and pipette tip 33, both indicated by dashed and dotted lines) can be moved above sample vessels located inside the thermal cycler 50, 52 in a position allowing a pipetting step to be conducted.

It should also be noted that in an advantageous embodiment, the closing device 54 does not extend into the area above the receiving plate 12 that is greater than the interval HP because of its essentially horizontal movement in an open setting. The direction of movement of the closing device 54 to the left (away from the receiving plate) shown for example in FIG. 1 is advantageous because the closing device does not protrude into the usable area of the receiving plate 12 when it is in the open setting. Of course, however, other directions of movement, e.g. in the direction of the X axis, are also possible. One can also conceive of a kind of retractable closing device divided into a plurality of segments that are retractable with respect to one another and can be moved downward along the thermal cycler housing inside or outside the housing in order to make the interior of the thermal cycler freely accessible. The one-piece embodiment of the closing device 54 shown in the example is also only optional. The closing device may also consist of two pieces, each of which can cover half of the interior space and be moved in the same or opposite directions, and if necessary, slide over each other. Moreover, it is also advantageous to automatically move the closing device 54 between its open and closed settings by means of a corresponding drive component.

It can also be seen from FIG. 2 that a thermal cycler 50' having a larger construction height can be used. This type of thermal cycler would have to be mounted in a notch (e.g., notch 72 shown in FIG. 4) in the receiving plate 12 so that a lower part 51' of the thermal cycler 50', indicated by a dotted line, can be configured below the receiving plate 12. In such cases as well, however, it is particularly advantageous for the sample handling system 10 if the highest point 58 of the thermal cycler 50' shows a shorter interval H (FIG. 3) from the receiving plate 12 than the interval HP (FIG. 3). The maximum interval HP between the lower end of at least one pipette tip 33 and the receiving plate 12 is approximately 100 mm to 180 mm, and preferably approximately 125 mm to 150 mm. The highest point 58 of the upper surface of the thermal cycler 50, 50', 52 thus shows a interval H from the receiving plate 12 of approximately 95 mm to 175 mm, and preferably approximately 120 mm to 145 mm.

In order to move sample vessel carriers (PCR plates) inside a thermal cycler or remove them therefrom, a gripping mechanism (not shown) may also be provided on the working arm 14 or extension arm 18. For example, this kind of gripping mechanism may be composed of two grippers that can be installed on pipetting channels 32 instead of pipette tips so that these two gripper-pipetting channels can be used to pick up and transport a sample vessel carrier. As soon as this transportation of sample vessel carriers is completed, the grippers can be placed in a ready position at particular location on the receiving plate, and the pipetting channels can once again be fitted with pipette tips. Of course, a gripping mechanism separate from one of the pipetting channels may also be used. Another possibility would be a gripping mechanism configured outside of the receiving plate, which, however, would at least partially reach the usable area of the receiving plate.

The following is a description of workflows I-III, which require a PCR mechanism equipped with a closing device (lid) 54 that can be used at any desired time during the PCR or incubation process. In these workflows, it is advantageous to use a sample handling system 10 such as that shown in FIGS. 1 to 3. The total workflow described is only an example, and comprises a PCR reaction (Workflow I), a cleaning (clean-up) step (Workflow II), and the implementation of a sequencing reaction (Workflow III). In all of these workflows, the required pipetting steps are carried out in the area of the thermal cycler 50, i.e., in sample vessels inside the thermal cycler. It is not necessary to remove the sample vessels or sample vessel carriers from the thermal cycler or move them to another position for the purpose of pipetting. As the closing device 54 can be opened at any time during a temperature step, it is possible, as shown in Workflow I for example, to carry out so-called hot start PCR. A clean-up-process (Workflow II) can also be directly carried out on the thermal cycler without the need to remove the sample vessels or the accompanying sample vessel carrier from the thermal cycler. According to Workflow III, an aliquot of the purified PCR product can be pipetted into other sample vessels of another sample vessel carrier, with the other sample vessel carrier automatically being placed in a second thermal cycler located in the area of the receiving plate (e.g. thermal cycler 52). The cycle sequencing reaction is then pipetted and the relevant program is run through. Alternatively, an aliquot of the (unpurified) PCR product (according to Workflow I) is directly pipetted into other sample vessels of another sample vessel carrier in a second thermal cycler. The clean-up-process is then directly carried out on the second thermal cycler, followed by sequencing of this purified aliquot in the second thermal cycler.

Figure 4:
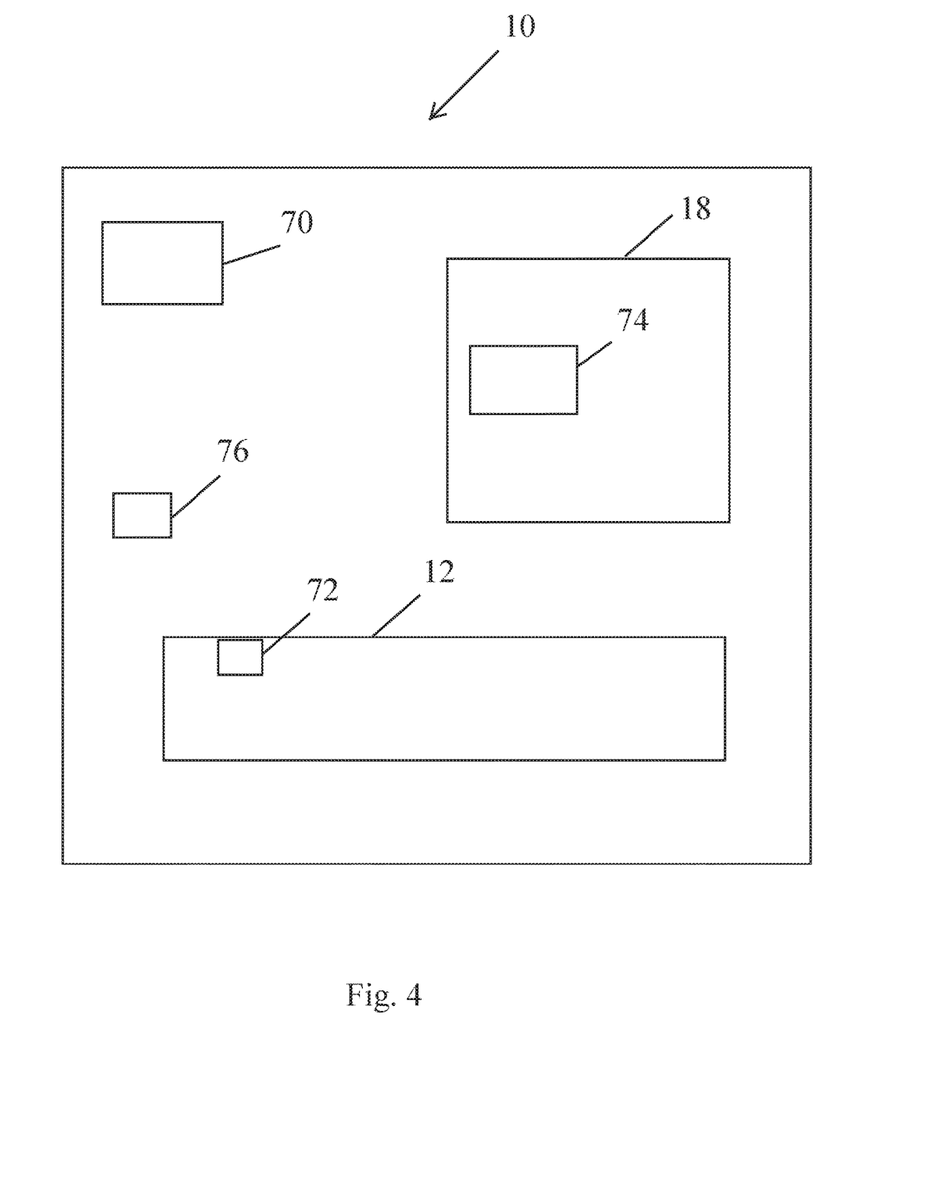
FIG. 4 shows a labeled representation of an exemplary sample handling system according to embodiments of the present invention.

Workflow I, referred to as "Hot-Start PCR," may take place as follows:

1. Closing device (lid) 54 of the thermal cycler 50 is opened.
2. An empty PCR plate (sample vessel carrier) is placed in the opened thermal cycler 50 by the automated gripping mechanism in such a manner that it is configured in the area of the receiving plate 12 in a so-called "on deck" position.
3. Addition of sample liquid and PCR components (Mastermix, primer) by means of the pipetting mechanism 30.
4. Starting of the first phase of the PCR reaction profile at 95° C. for denaturing.
5. When the temperature is greater than the annealing temperature of the primer, the Taq polymerase or some other essential component of the PCR reaction mixture is dispensed into the sample vessels (wells) by means of the pipetting mechanism 30.
6. Typically, a small volume (approximately 1-2 μL) is dispensed into the sample vessels. Because of the high temperature of the liquid in the sample vessels, dispensing is supported by a control/regulation system based on the pressure in the pipetting channel 32 (such as the MAD or ADC systems known from the applicant) in order to achieve efficient delivery (dispensing) of the small amount of Taq polymerase and prevent any sample liquid from penetrating into the (disposable) pipette tip when the pipette tip 33 moves out of the sample liquid.
7. As a rule, the denaturing process requires 2 minutes. Depending on the configuration of the pipetting mechanism 30 with pipetting channels 32, the Taq polymerase (or some other essential component of the PCR reaction mixture) is to be dispensed simultaneously in as many sample vessels as possible. Ideally, a PCR plate (sample vessel carrier) with 96 wells (sample vessels) is used, with a pipetting mechanism 30 having 8 pipetting channels 32 being employed.
8. After this pipetting step, the PCR plate (sample vessel carrier having the sample vessels) is covered with a sealing mat (sealing element)(e.g., sealing element 76 as shown in FIG. 4), and the closing device of the thermal cycler is automatically closed.
9. The cycles of the PCR process are conducted; for example, the following temperature profile is run through 30 times: 15 sec. at 95° C., followed by 30 sec. at the annealing temperature, which depends on the primer used, followed by a polymerisation step of the nucleic acid sequence to be polymerised at 72° C. for one min. per 1 kb (1000 base pairs).

Workflow II, referred to as "Removal of unincorporated dNTP and primer by Exo SAP IT," can be described as follows:

1. After the PCR reaction is completed, the closing device 54 is opened, and the sealing element is removed.
2. Exo SAP IT (Registered Trademark of Affymetrix Inc.) is used so as not to destroy unincorporated primer and dNTPs. 2 μL of Exo SAP IT per 5 μl of PCR reaction solution is added to each sample vessel by means of the pipetting mechanism 30.
3. The sealing element is placed on the PCR plate (sample vessel carrier), and the closing device 54 of the thermal cycler 50 is closed.
4. Incubation at 37° C. for 15 min. in order to purify (clean-up) the PCR.
5. Incubation at 80° C. for 15 min. in order to destroy the Exo SAP IT enzyme.
6. Cooling off of the reaction.

Workflow III may take place as follows:
1. After purification (clean-up), the closing device 54 of the thermal cycler 50 is opened, and the sealing element is removed.
2. A required amount of the PCR product is pipetted into another empty PCR plate that is inside a second thermal cycler 52 configured adjacent to/on the receiving plate 12.
3. The cycle sequencing reaction mixture "BigDye Terminator" (Registered Trademark of the firm Life Technologies) is pipetted onto the samples (specimens) taken.
4. A sealing element is placed on the PCR plate, and the closing device 54 of the second thermal cycler 52 is closed.
5. The cycle-sequencing program is conducted using the second thermal cycler 52.

Finally, it should be noted that the sample handling system 10 also includes a control mechanism (e.g., control mechanism 70 shown in FIG. 4) that is not shown and not described in further detail, such as a computer that can be used to activate all of the movements of the pipetting mechanism and a gripping mechanism(e.g., gripping mechanism 74 shown in FIG 4.). The control mechanism (e.g., control mechanism 70) can also activate the thermal cycler(s) 50, 50', 52 in order to run desired cycles. Alternatively, the control mechanism (e.g., control mechanism 70) may be connected via a corresponding interface (e.g., interface 11) to an internal control/regulation unit of the thermal cycler. The movable components, such as the working arm, pipetting mechanism, pipetting channels, gripping mechanism (e.g., gripping mechanism 74), and closing device of the thermal cycler, are operated by means of suitable drive units, and these drive units may also be activated by the control mechanism (e.g., control mechanism 70).

The sample handling system described allows integrated conduct of the PCR process, including all of the pipetting steps that must be carried out during the PCR process. It is also possible for sample vessels used in the PCR process to remain inside the thermal cycler when pipetting steps are required. The entire process can therefore be carried out more automatically and efficiently.

The invention claimed is:

1. A sample handling system for the handling of chemical or biological samples, the system comprising:
   a dosing device:
   with a receiving plate, wherein the receiving plate is configured in an essentially horizontal position in a plane defined by a first and a second axis;
   at least one working arm that is movable in the direction of the first axis relative to the receiving plate, and wherein the working arm extends in the direction of the second axis above the receiving plate;
   at least one pipetting mechanism that is movable in the direction of the second axis is mounted on the working arm, the at least one pipetting mechanism comprising at least one pipetting channel that is movable in the direction of a third axis orthogonal to the direction of the first and second axes and has a pipette tip mounted or mountable thereon, and the at least one pipetting mechanism is configured so as to dispense or aspirate liquid into or out of one or more sample vessels,
   a sample vessel carrier containing the one or more sample vessels;
   a sealing element configured to seal the sample vessels and wherein the sealing element is removable to allow a pipetting step to be carried out in the sample vessels;
   at least one thermal cycler that is provided on the receiving plate;
   a gripper mounted on the working arm that is movable in the direction of the first, second and third axes is mounted on the working arm and configured to remove the sealing element from the at least one thermal cycler and transport the sample carrier within the system; and
   a controller configured to control the function of the dosing device and thermal cycler such that the pipetting mechanism is movable in a position above the sample vessels in the thermal cycler in a setting that further allows the pipetting step to be carried out into the sample vessels in the thermal cycler by the pipetting mechanism in the position above the sample vessels in the thermal cycler during a PCR process in that the gripper is movable in a position above the sample vessels in the thermal cycler to remove and/or replace the sealing element and transport the sample carrier within the system.

2. The sample handling system according to claim 1, wherein the thermal cycler is mounted in an opening made in the receiving plate in such a manner that a lower surface of the thermal cycler is located below the receiving plate, wherein a highest point of the thermal cycler is located below a maximum possible interval between a lower end of at least one pipette tip and the surface of the receiving plate, with the interval making it possible for the pipetting mechanism or pipetting channels to move in the direction of a third axis.

3. The sample handling system according to claim 1, wherein the maximum possible interval between the lower end of at least one pipette tip and the surface of the receiving plate is approximately 100 mm to 180 mm.

4. The sample handling system according to claim 1, wherein the thermal cycler is provided with a lid-like closing device for covering the sample vessels inside the thermal cycler, wherein the closing device is movable relative to the thermal cycler in a direction that is essentially parallel to the receiving plate between an open setting in which the interior of the thermal cycler is freely.

5. The sample handling system according to claim 4, wherein the control mechanism is configured in such a manner that the closing device of the thermal cycler is moved into its open or closed setting based on the position of the pipetting mechanism relative to the thermal cycler.

6. The sample handling system according to claim 5, wherein the control mechanism is configured such that the closing device is moved to its open setting when a step of pipetting into the sample vessels inside the thermal cycler is carried out by means of the pipetting mechanism and such that the closing device is moved to its closed setting after the step of pipetting into the sample vessels inside the thermal cycler is completed.

7. The sample handling system according to claim 1, further comprising a gripping mechanism that is movable in the directions of the first, second, and third axes relative to the receiving plate, wherein the gripper mechanism is activated by the control mechanism, and is configured so as to grip a sample vessel carrier and transport the sample vessel carrier to desired positions on the receiving plate.

8. The sample handling system according to claim 7, wherein the gripping mechanism is configured so as to displace sample vessels inside or remove sample vessels from the thermal cycler.

9. The sample handling system according to claim 7, wherein the gripping mechanism is placed on the working arm or provided on an additional movable working arm that is movable relative to the receiving plate.

10. The system according to claim 1, wherein the working arm is movable along a first edge of the receiving plate.

11. The sample handling system according to claim 1, wherein the maximum possible interval between the lower end of at least one pipette tip and the surface of the receiving plate is approximately 125 mm to 150 mm.

12. The sample handling system according to claim 1, wherein said functions of the dosing device that the control mechanism is configured so as to activate or control include at least one of a movement in the directions of the three axes and aspiration or dispensing of liquid by means of the pipetting mechanism.

13. The sample handling system according to claim 1, wherein said functions of the thermal cycler that the control mechanism is configured so as to activate or control include carrying out cycles in a PCR process.

14. A process for the control of a sample handling system by means of its accompanying control mechanism comprising;
providing the sample handling system of claim 1,
opening the closing device of the first thermal cycler;
displacing the first sample vessel carrier containing sample vessels inside the first thermal cycler by means of the gripping mechanism, with the sample vessels being filled with sample liquid or unfilled; and
conducting a PCR process, wherein the closing device of the first thermal cycler is opened or closed based on the steps of the PCR process to be conducted, and
wherein, based on the setting of the closing device, additional components are dispensed by the pipetting mechanism to the sample vessels inside the first thermal cycler during the PCR process.

15. The process according to claim 14, further comprising automatically moving or removing a sealing element that seals the sample vessels on the first sample vessel carrier, based on the PCR process and the setting of the closing device.

16. The process according to claim 15, wherein after completion of a specified step of the PCR process, the closing device of the first thermal cycler is opened, the sealing element placed on the sample vessels is removed, and processed sample liquid is aspirated from the sample vessels by means of the pipetting mechanism and dispensed into additional sample vessels outside the first thermal cycler.

17. The process according to claim 16, further comprising dispensing a further component in sample vessels contained inside at least one of the first and a second thermal cycler by means of the pipetting mechanism.

18. The process according to claim 14, further comprising filling the sample vessels with sample liquid to be analysed by means of the pipetting mechanism.

19. The process according to claim 14, further comprising filling the sample vessels with further components required for analysis including at least one of a primer, polymerase, and water, by means of the pipetting mechanism.

20. The process according to claim 15, wherein the sealing element includes a sealing mat.

21. The process according to claim 16, wherein the additional sample vessels are located in a second sample vessel carrier that is placed in a second thermal cycler or on a receiving plate.

* * * * *